United States Patent
Grubbs

(10) Patent No.: US 6,679,921 B2
(45) Date of Patent: Jan. 20, 2004

(54) SHUTTLE LOCK PROSTHETIC CONNECTOR

(76) Inventor: Robert Grubbs, 10546 158 North, Jupiter, FL (US) 33478

(*) Notice: Subject to any disclaimer, the term of this patent is extended or adjusted under 35 U.S.C. 154(b) by 47 days.

(21) Appl. No.: 10/058,705

(22) Filed: Jan. 28, 2002

(65) Prior Publication Data

US 2003/0144744 A1 Jul. 31, 2003

(51) Int. Cl.$^7$ ............... A61F 2/60; A61F 2/80
(52) U.S. Cl. ........................ 623/33; 623/36
(58) Field of Search ............... 623/33, 36, 27, 623/32, 34, 35, 38, 37

(56) References Cited

U.S. PATENT DOCUMENTS

| | | |
|---|---|---|
| 4,564,365 A | 1/1986 | Winer et al. |
| 5,326,352 A | 7/1994 | Ferrier |
| 6,334,876 B1 * | 1/2002 | Perkins ................ 623/34 |
| 6,511,513 B1 * | 1/2003 | Laghi ................ 623/33 |

* cited by examiner

*Primary Examiner*—Corrine McDermott
*Assistant Examiner*—Alvin Stewart
(74) *Attorney, Agent, or Firm*—McHale & Slavin, P.A.

(57) ABSTRACT

A prosthetic connector includes a cylindrical housing having a semi-toroidal top surface and a flat bottom surface with a mated pin receiving aperture extending axially therethrough and a diametrically positioned cavity therein. The flat bottom surface of the connector is mounted to a prosthetic. A shuttle lock latch is slidingly disposed in the cavity, and the connector includes a means for biasing the shuttle lock latch wherein a portion of latch is available to positively secure a mated pin inserted into the pin receiving aperture. The prosthesis includes an actuator means for releasing the pin. The shuttle lock latch is securable to the pin by engagement of the shuttle lock latch, and the connector is manually releasable by means of the actuator.

9 Claims, 7 Drawing Sheets

SHUTTLE LOCK PROSTHETIC CONNECTOR

FIELD OF THE INVENTION

This invention relates generally to the field of prosthetic limbs, and more particularly to an improved prosthetic connector having a shuttle lock mechanism which enables easy and rapid connection and disconnection of a prosthetic limb from an amputation site.

BACKGROUND OF THE INVENTION

Artificial limbs adapted to reproduce the form or function of a lost member are very common. Early artificial limbs were formed as integral pieces which were permanently affixed to the amputation site. In the practice of modern prosthetics, a connector assembly is permanently attached to the amputation site, which allows the user to remove the prosthesis when desired. The connector assembly also allows the user to have interchangeable prosthetic limbs.

Newer prosthetic limbs can be constructed for specialized uses, such as athletics. For example, the user of such limbs may wish to wear a more esthetically pleasing limb for social occasions, and then switch to a specialized athletic prosthesis for engaging in physical activities. The user may also wish to change the prosthesis to an inexpensive, durable prosthesis to protect the main prosthesis from damage, such as while showering or swimming. It is therefore highly desirable to provide a prosthetic connector assembly which facilitates rapid and easy removal and reattachment of the prosthesis.

There are numerous examples of prosthetic connector assemblies in the prior art. Connector assemblies designed for rapid coupling include Ferrier, U.S. Pat. No. 5,326,352 and Weiner et al., U.S. Pat. No. 4,564,365. The Winer et al. system is described as a "quick change" mechanism, however the Ferrier mechanism requires the user to perform several steps. Another drawback of the Ferrier system is the relatively large number of moving parts. A disadvantage of the Ferrier device is the use of a removable pin to lock the prosthesis into place, which can become lost.

There remains a need in the art for an improved prosthetic connector assembly which allows rapid connection and removal having a simplified design with a minimal number of moving parts.

SUMMARY OF THE INVENTION

It is an objective of the invention to provide a socket for a prosthetic connector assembly which enables a user to rapidly and easily remove and reattach a prosthesis.

It is another objective to provide a socket for a prosthetic connector assembly which is self-guiding.

Yet another objective is to provide a connector having a latch lock that includes a wear latch that maintains a secure lock despite the amount of wear that occurs upon the latch lock.

It is still another objective to provide a socket for a prosthetic connector assembly which permits the user to readily interchange different types of prostheses.

It is a further objective of the invention to provide a socket for a prosthetic connector assembly having a simplified design with a minimal number of moving parts.

In accordance with the above objectives, an improved shuttle lock socket for a prosthetic connector assembly is provided. The socket is mounted to the prosthesis, and securely receives a pin. The shuttle lock mechanism is configured to be self-locking by the action of inserting the pin. The pin can be quickly and easily removed by depressing a release button which displaces the spring-biased shuttle lock mechanism. The prosthetic connector includes a cylindrical housing having a semi-toroidal top surface and a flat bottom surface with a mated pin receiving aperture extending axially therethrough and a diametrically positioned cavity therein. The flat bottom surface of the connector is mounted to a prosthetic. A shuttle lock latch is slidingly disposed in the cavity, and the connector includes a means for biasing the shuttle lock latch wherein a portion of latch is available to positively secure a mated pin inserted into the pin receiving aperture. The means for biasing the shuttle lock latch can be a spring. The prosthesis connector of the present invention includes an actuator means for releasing the pin. The shuttle lock latch is securable to the pin by engagement of the shuttle lock latch, and the connector is manually releasable by means of the actuator.

The cylindrical housing has a diameter defining a top and a bottom. The housing is preferably constructed from adjoined first and second sections which are generally cylindrical. The first section has generally planar front and rear surfaces wherein the front surface is positioned in the interior of the housing and the rear surface forms the rear surface of the housing. The second section has a planar rear surface positioned in the interior of the housing, and the front surface of the first section has an elongated recess positioned along the diameter wherein so that the aperture is centered in the elongated recess. The elongated recess is generally rectangular and has a top surface, a bottom surface, and opposing side surfaces, so that the elongated recess cooperates with the rear surface of the second section to form the interior cavity when the first and second sections are adjoined.

The shuttle lock latch is generally rectangular and has a top end surface, a bottom end surface, a planar front surface and a planar rear surface and a width providing close sliding engagement with the opposing sides of the elongated recess. A pin-receiving opening extends through the shuttle lock latch. The pin-receiving opening has a first perimeter coincident with the front surface of the shuttle lock latch and a second perimeter coincident with the rear surface of the shuttle lock latch. The first perimeter is larger than the second perimeter, and the first perimeter and second perimeter have upper and lower edges, wherein the uppers edges are aligned to be equidistant from the top face of the shuttle lock latch and the lower edges define a linearly inclined surface within the pin receiving opening adjacent to the lower perimeter. The shuttle lock latch is slidable between a plurality of positions within the elongated recess. The pin-receiving opening is centrally aligned with the aperture when the bottom rear end of the shuffle lock latch contacts the bottom surface of the elongated recess. In operation, the act of urging a pin into the aperture causes the pin to contact the linearly inclined surface and continuously displace the shuttle lock latch towards the bottom surface until the pin extends through the aperture. The first section of the socket for a prosthetic connector includes a through-bore which extends along the diameter through the top surface of the elongated recess to the first section.

The connector further includes a plunger assembly which extends perpendicularly from and is fixedly attached to the top face of the shuttle lock latch. The plunger assembly comprises a plunger rod and a pushbutton member fixedly attached to at the distal end of the plunger rod. The plunger rod extends through the through-bore of the first section, whereby urging the plunger assembly downwardly displaces the shuttle lock latch. The bottom surface of the elongated recess includes a spring-receiving bore therein along the diameter. The spring member extends into the spring receiving bore, wherein the spring member can be compressed into the spring-receiving bore. The act of urging plunger assembly downwardly displaces the shuttle lock latch to release the pin.

The socket further includes a means to attach the first section to the second section. The attachment means preferably comprises a plurality of threaded through-bores in the first section which can be aligned with plurality of threaded bores in the second section, wherein the first section can be secured to the second section by means of threaded screws. A plurality of threaded bores is also provided to attach the socket to a prosthesis.

DETAILED DESCRIPTION OF THE INVENTION

Although the invention will be described in terms of a specific embodiment, it will be readily apparent to those skilled in this art that various modifications, rearrangements, and substitutions can be made without departing from the spirit of the invention. The scope of the invention is defined by the claims appended hereto.

Figure 1:
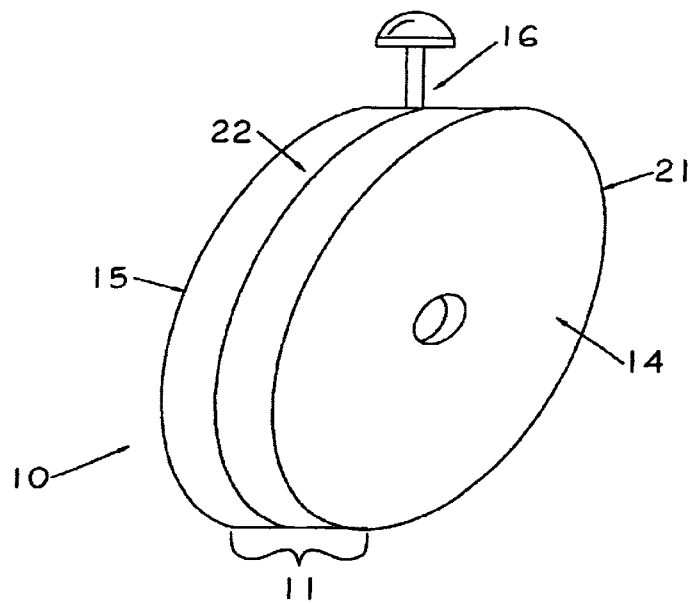
FIG. 1 is a perspective view of the socket portion of a prosthetic connector assembly according to a preferred embodiment of the invention.
Figure 2:
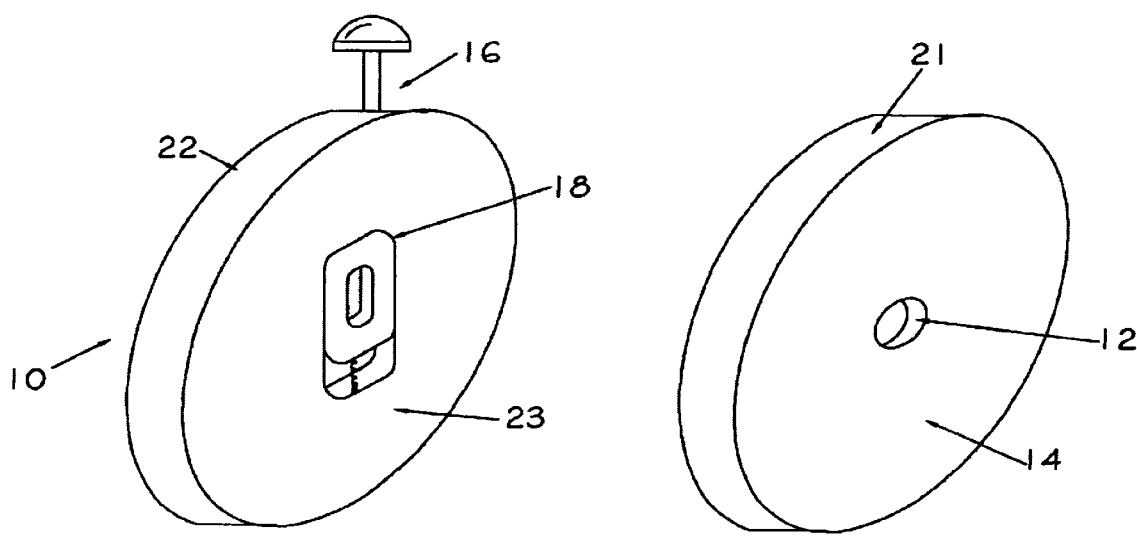
FIG. 2 is an exploded view of the partially disassembled socket of FIG. 1.

FIG. 1 illustrates a perspective view of the prosthetic connector 10 of the invention. An exploded view of the partially disassembled prosthetic connector 10 is shown in FIG. 2. The prosthetic connector 10 includes a cylindrical housing 11 having a semi-toroidal top surface 14 and a flat bottom surface 15. In use, the flat bottom surface 15 is mounted to a prosthetic. The housing 11 can be constructed first section 21 and a second section 22. The prosthetic connector 10 includes an aperture 12 extending axially through the housing which receives and secures a pin (not shown). The top surface 14 is contoured as a semi-toroid about the aperture 12 to effectively guide the pin into the aperture 12. A shuttle lock latch 18 is slidingly disposed in a diametrically positioned interior cavity within the housing. The prosthetic connector 10 includes a means for biasing the shuttle lock latch 18 so that a portion of the shuttle lock latch 18 positively secures the pin in the aperture. An actuator means is provided for releasing the pin by either depressing or pulling the actuator means. In the preferred embodiment, the actuator means is the pushbutton plunger assemby 16.

Figure 3:
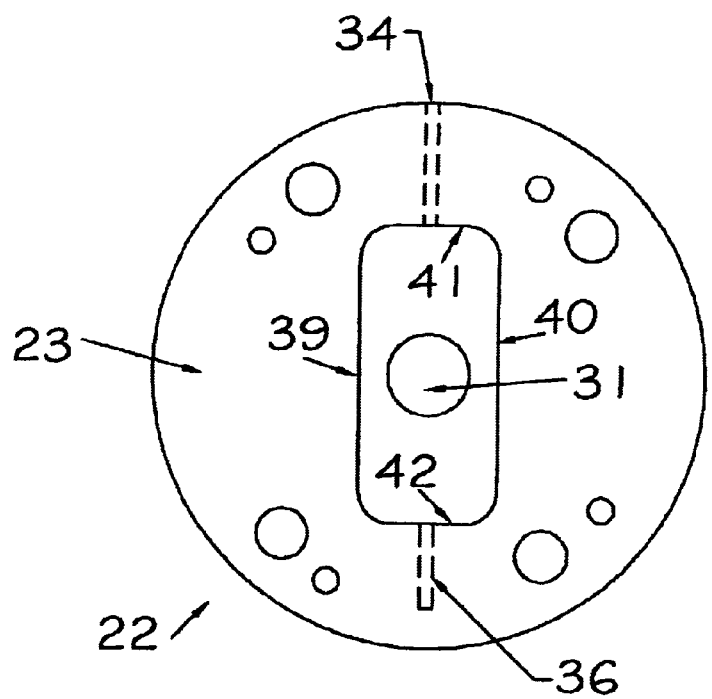
FIG. 3 illustrates a front view of the rear section of the socket of FIG. 1, with the shuttle lock assembly removed.
Figure 4:
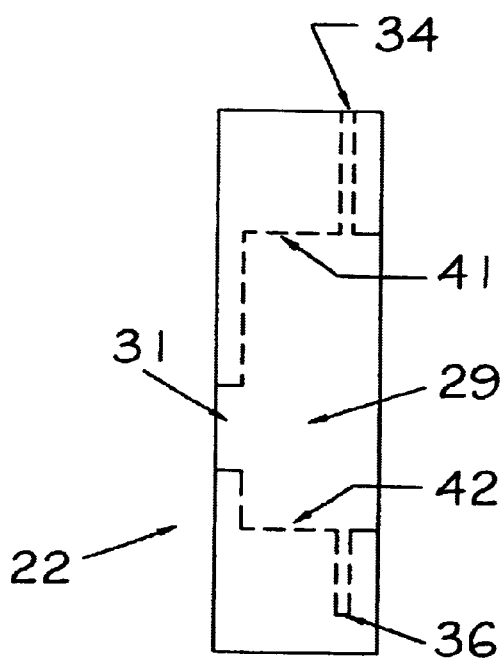
FIG. 4 illustrates a side view of the rear section shown in FIG. 3.

FIGS. 3 and 4 respectively illustrate a front view and a side view of the second section 22 with the shuttle lock assembly 18 removed for ease of illustration. The front surface 23 of second section 22 includes an elongated recess 29 (which forms the cavity for the shuttle lock latch 18 when the first and second sections 21, 22 are adjoined). The elongated recess 29 has left and right sides 39, 40 and top and bottom sides 41, 42. An aperture 31 is located within the elongated recess 29. In the preferred embodiment, the elements of the actuator are received in through-bore 34 and a spring-receiving bore 36. The through-bore 34 extends perpendicularly upward from the top side 41 of the elongated recess 29 to the front surface 23 of second section 22. The bore 36 extends perpendicularly downward from the bottoms side 42 of the elongated recess 29.

Figure 5:
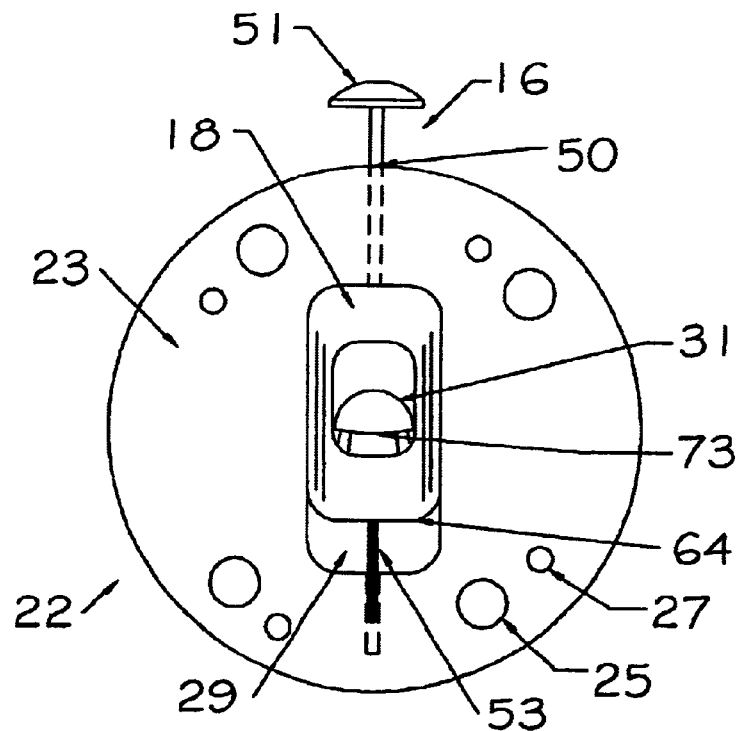
FIG. 5 illustrates a front view of the rear section of the socket of the preferred embodiment with the shuttle lock assembly installed therein.
Figure 6:
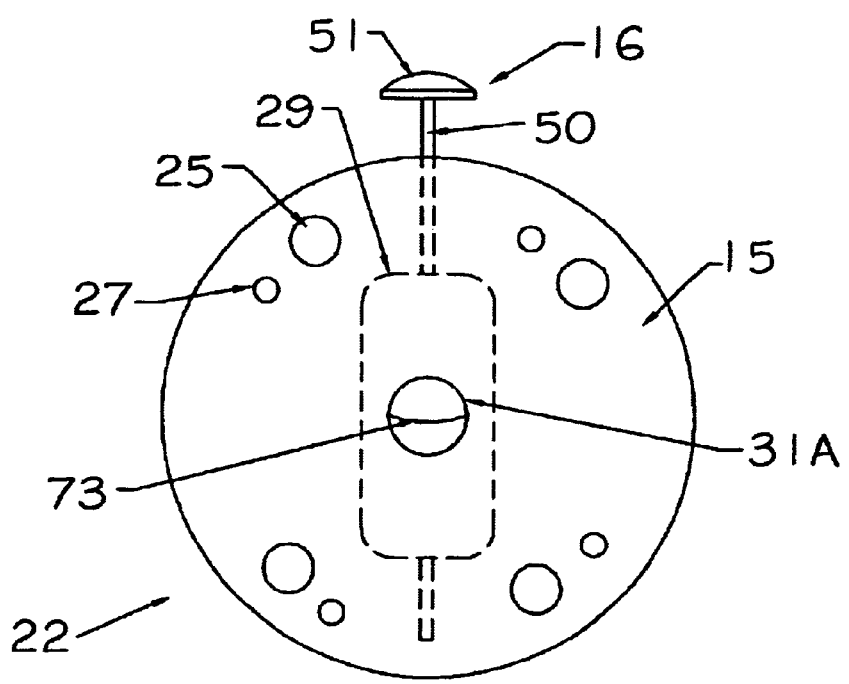
FIG. 6 illustrates a back view of the rear section of the socket, as shown in FIG. 5.

FIGS. 5 and 6 illustrate front and back views of the second section 22 with the shuttle lock latch 18 and plunger assembly 16 installed therein. The second section 22 has a bottom surface 15 which, in use, is adjoined to amputation site or a prosthesis, and a front surface 23 which is adjoined to first section 21. The second section 22 includes a plurality of threaded bores 25 whereby the prosthetic connector 10 can be fixedly attached to a prosthesis using threaded screws. In addition to threaded screws, any suitable attachment method can be used. The plurality of threaded bores 27 are used to attach the second section 22 to the first section 21 by means of threaded screws.

Figure 7:
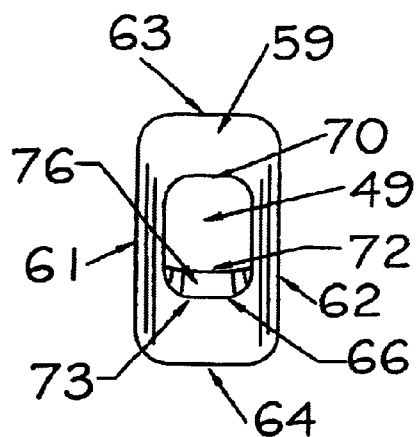
FIG. 7 illustrates a front view of the shuttle lock latch of the preferred embodiment of the invention.
Figure 8:
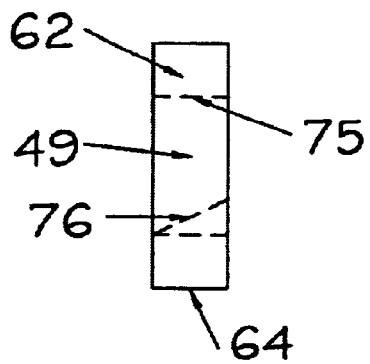
FIG. 8 illustrates a side view of the shuttle lock latch shown in FIG. 7.
Figure 9:
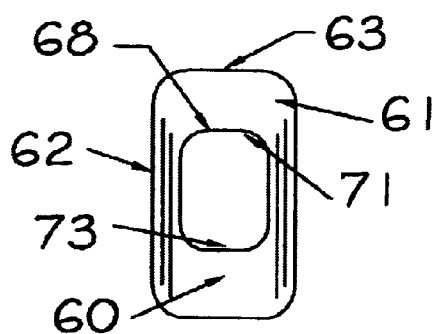
FIG. 9 illustrates a rear end view of the shuttle lock latch shown in FIG. 7.

The shuttle lock latch 18 which is slidably disposed in the elongated recess 29. The shuttle lock latch 18 is shorter in length than the elongated recess 29 and has a width sized for close, sliding engagement with the left and right sides 39, 40 of he elongated recess 29. The configuration of the shuttle lock latch 18 is shown in detail in FIGS. 7–9, which illustrate front, side and rear views respectively. The shuttle lock latch 18 has a front face 59, rear face 60, opposing left and right side faces 61, 62, and opposing top and bottom faces 63, 64. The depth of the shuttle lock latch 18 (i.e. from front to back) is preferably approximately equal to the depth of the elongated recess 29. The shuttle lock latch 18 has a pin-receiving opening 49 extending from front face 59 to rear face 60. The pin-receiving opening 49 has a first perimeter 66 coincident with front face 59 and a second perimeter 68 coincident with rear face 60. The configuration of the first and second perimeters 66 and 68 are preferably approximately rectangular with rounded corners. The first perimeter 66 is larger than second perimeter 68. The first and second perimeters 66 and 68 respectively have top edges 70, 71 and lower edges 72, 73. The top edges 70, 71 are aligned so as to be equidistant from top face 63, defining an inside top surface 75 of pin-receiving opening 49 which is substantially perpendicular to front and rear surfaces 59, 60. The position of lower edges 72, 73 define a substantially linearly inclined inside lower surface 76 of pin-receiving opening 49. In use, a pin can be grasped between the lower edge 73 and the upper peripheral edge 31a of aperture 31.

Referring again to FIG. 5, it is seen that a helical spring 53 is fixedly attached to the bottom surface 64 of shuttle lock latch 18. The spring 53 extends downwardly into the bore 56 in second section 22. The spring 53 has sufficient tension to bias the shuttle lock latch 18 in an upward position against the top side 41 of the elongated recess 29. The pushbutton plunger assembly 16 includes a plunger 50 which is fixedly attached at the top surface 63 of shuttle lock latch 18. The plunger 50 extends through the through-bore 34 in second section 22, and has a push-button 51 fixedly attached at the distal end of plunger 50.

Figure 10:
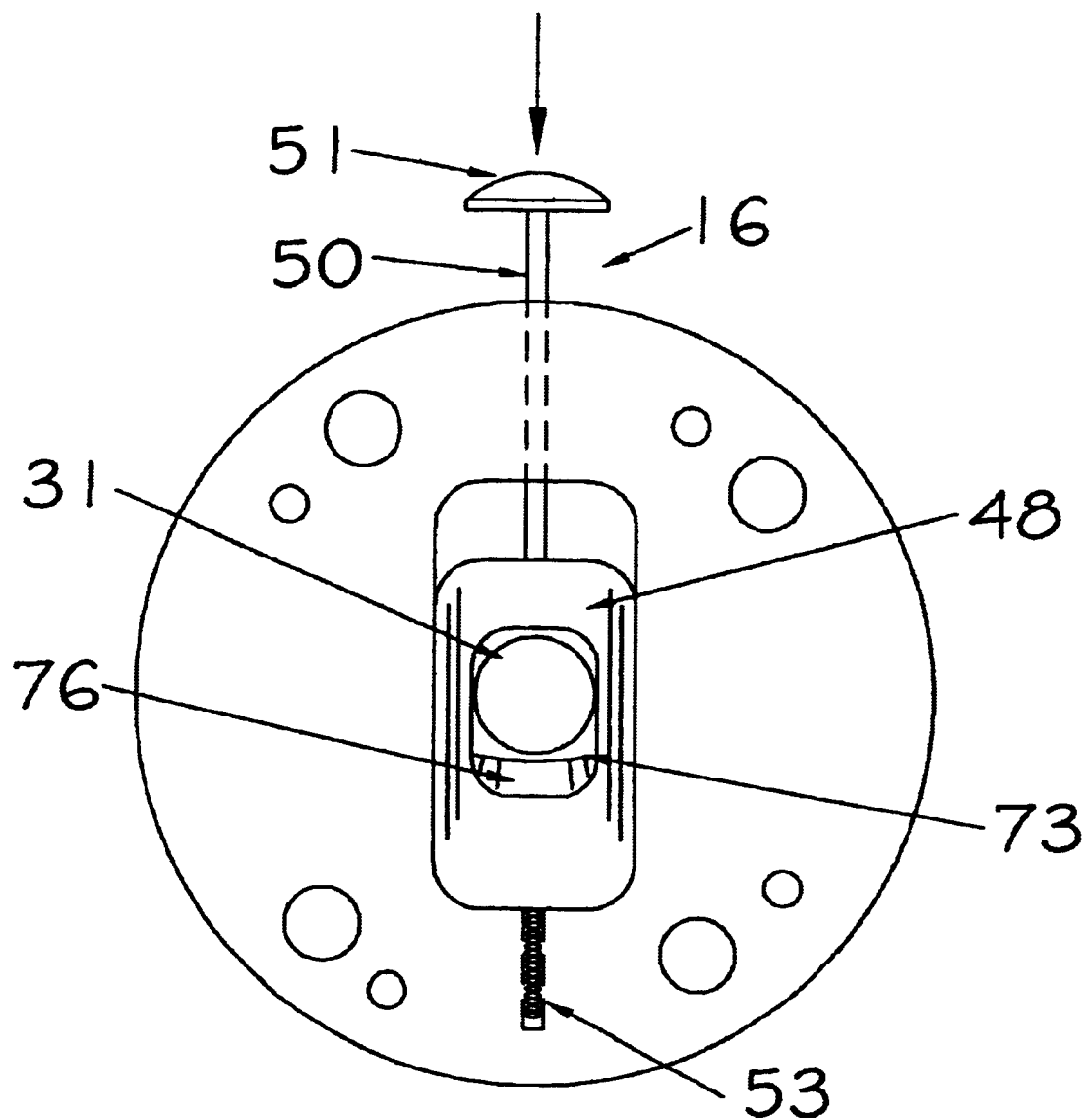
FIG. 10 illustrates the socket shown in FIG. 5 in which the button and plunger assembly has been fully depressed.

FIG. 10 illustrates the plunger 50 in a fully depressed position which urges the shuttle lock latch 18 downwardly in the elongated recess 29 against the biasing of the spring 53. It can be seen that the bottom face 64 of the shuttle lock latch 18 is now flushly aligned with the bottom surface 42 of the elongated recess 29. The spring 53 is fully depressed into the bore 36. The second perimeter 68 is centrally aligned with the aperture 31 to allow insertion of a pin.

Figure 11A:
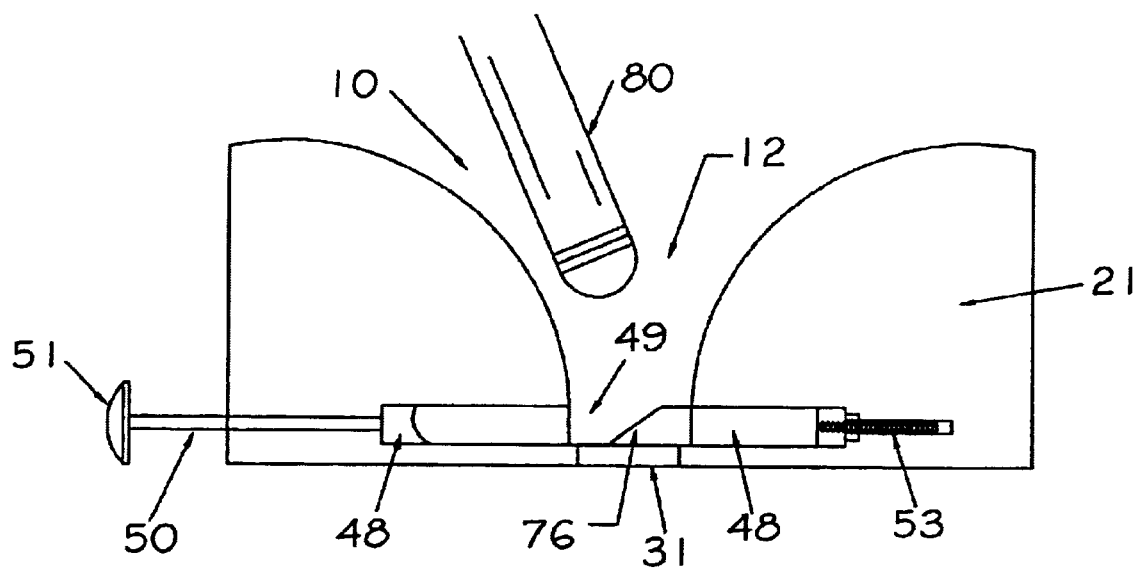
FIG. 11a illustrates a cross-sectional view of the socket according to the invention showing the insertion of a pin.
Figure 11B:
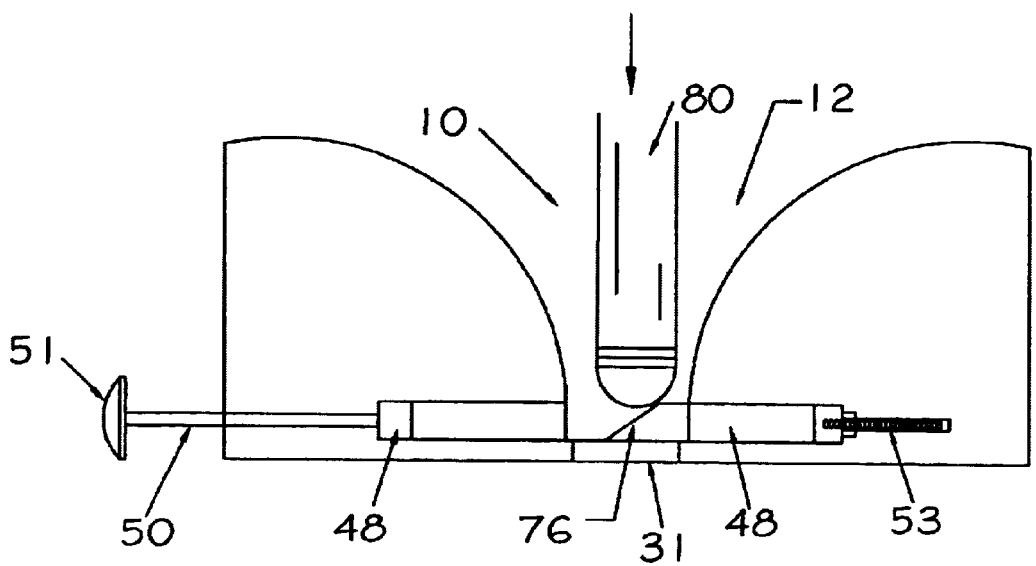
FIG. 11b is a cross-sectional view of the socket of FIG. 11a showing the pin contacting the shuttle locket latch.
Figure 11C:
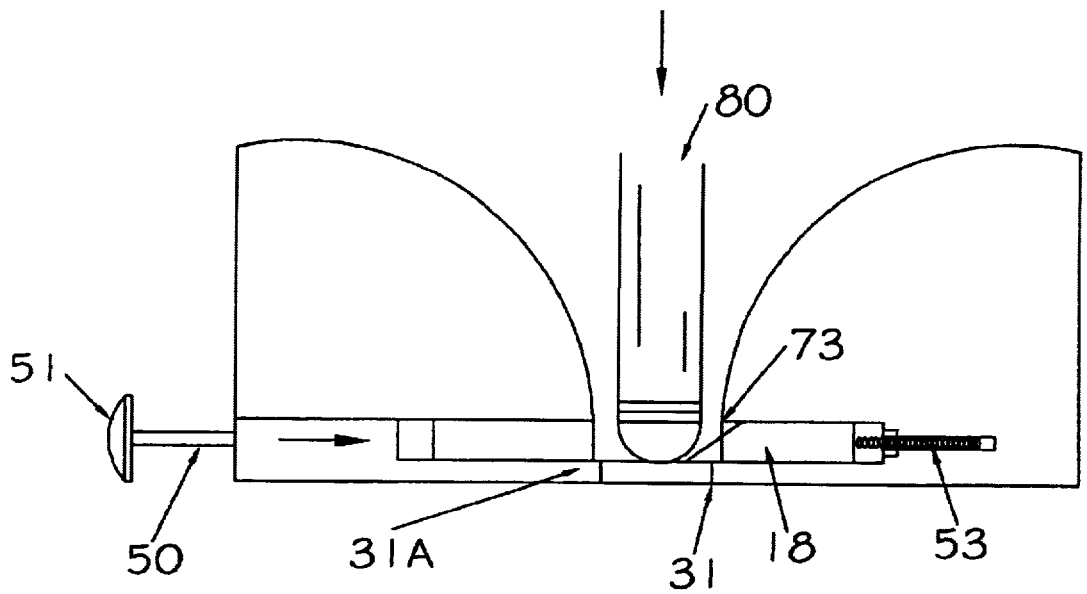
FIG. 11c illustrates the lateral displacement of the shuttle lock latch shown in FIG. 11a by insertion of the pin.
Figure 11D:
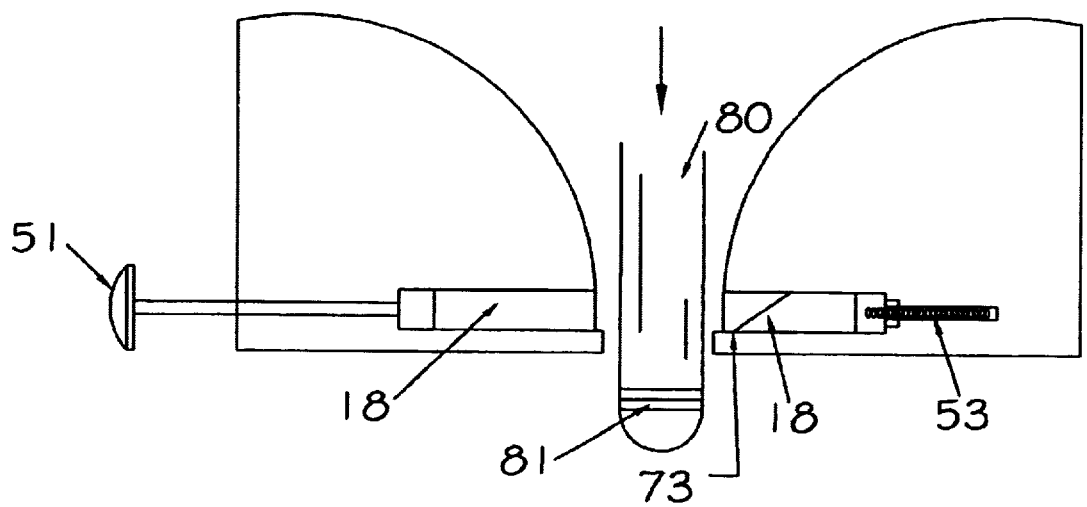
FIG. 11d illustrates the alignment of the shuttle lock latch opening and the aperture of the rear section.

FIGS. 11a–d are cross-sectional views of the fully assembled prosthetic connector 10 showing the operation of the prosthetic connector 10. The first section 21 has an aperture 32 for receiving a pin 80. The semi-toroidal contour of the front face 14 of the first section 21 serves to guide the pin 80 into the aperture 12 (FIG. 11a). Once the pin 80 has entered the aperture 12 (FIG. 11b), the pin 80 contacts the inclined inside lower surface 76 of the pin-receiving opening 49. When a user urges the pin 80 into the aperture 12, the linear incline of the lower surface 76 causes the shuttle lock latch 18 to be continuously displaced towards the bottom surface 42 of the elongated recess 29 by compression of the spring 53 (FIG. 11c). When fully compressed, the latch opening 49 is aligned with the aperture 31 and the pin 80 is then inserted through the aperture 31 (FIG. 11d). The spring 53 urges the shuttle lock latch 18 upwards, and the annular groove 81 of the pin 80 is secured between the lower edge 73 of the shuttle lock latch 18 and the upper peripheral edge 31a of aperture 31.

To release the pin 80, the button 51 is manually pressed until the latch opening 49 is aligned with the aperture 31, thus freeing the pin 80. The pin 80 can then be manually removed from the prosthetic connector 10. In an alternative arrangement, the shuttle lock latch 18 can be biased in the downward position by a spring mechanism coupled to the plunger 50. In this embodiment, the pin 80 is inserted and released by pulling the plunger outwardly.

The inventor has found that the semi-toroidal contour of the top surface 44 of first section 21, as shown in cross-section in FIGS. 11a–d, is particularly advantageous for guiding the pin 80 into the aperture 12. The inventive shape of the first section 21 makes the prosthetic connector 10 essentially self-guiding, so that one need not even see the pin 80 or the prosthetic connector 10 when a prosthetic is attached. This feature is useful when, for example, the prosthesis is being attached through the user's shirt sleeves or trouser legs. One problem that can be encountered with prior art prosthesis prosthetic connectors is that the repeated insertion of the pin causes wear around the edges. Over time, this wear can damage the prosthesis prosthetic connector, making it difficult to insert the pin. In contrast, the inventor has found that with the inventive shape of first section 21 the inevitable wear actually increases the effectiveness in guiding the pin into the prosthetic connector 10 of the present invention. With the contour of the first section 21, the repeated insertion of the pin "sculpts" the contour of the upper surface 44 to streamline it for optimum ease of use.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

I claim:

1. A prosthetic connector which receives a mated pin having at least one annular groove, comprising:
    a housing defining a top and a bottom, said housing constructed from first and second sections, said housing having an aperture extending axially through said first and second sections; wherein said first section has generally planar front and rear surfaces wherein said front surface is positioned in the interior of said housing and the rear surface forms the rear surface of said housing; said front surface of said first section having an elongated recess positioned along said diameter wherein said aperture is centered in said elongated recess; said elongated recess being generally rectangular and having a top surface, a bottom surface, and opposing side surfaces;
    a shuttle lock latch slidingly disposed in said elongated recess, said shuttle lock latch being generally rectangular and having a top end surface, a bottom end surface, a planar front surface and a planar rear surface; said shuttle lock latch configured to have a width providing close sliding engagement with the opposing sides of said elongated recess, said shuttle lock latch having a length less than said elongated recess; said shuttle lock latch having a pin-receiving opening extending therethough, said pin-receiving opening having a first perimeter coincident with said front surface and a second perimeter coincident with said rear surface, wherein said first perimeter is larger than said second perimeter, wherein said first perimeter and second perimeter have upper and lower edges wherein said upper edges are aligned to be equidistant from the top face of said shuttle lock latch and said lower edges define a linearly inclined surface within said pin receiving opening adjacent to said lower perimeter, said shuttle lock latch being slidable between a plurality of positions within said elongated recess; wherein said pin-receiving opening is centrally aligned with said aperture when said bottom rear end of said shuttle lock latch contacts said bottom surface of said elongated recess; and
    means for biasing said shuttle lock latch against said top surface of said elongated recess;
    whereby urging said pin into said aperture causes said pin to contact said linearly inclined surface and continuously displace the shuttle lock latch towards the bottom surface until said pin extends through said aperture, and said groove contracts a portion of said shuttle lock latch and said aperture, said biasing means displacing said shuttle lock latch to secure said pin between said shuttle lock latch and said aperture.

2. The prosthetic connector according to claim 1, further comprising an actuator means for releasing the pin.

3. The prosthetic connector according to claim 1, wherein said means for biasing said shuttle lock latch comprises a spring.

4. The prosthetic connector according to claim 1, wherein said first section includes a through-bore extending along said diameter extending through said top surface of said elongated recess to said top of said first section.

5. The prosthetic connector according to claim 1, wherein said actuator means comprises a plunger assembly extending perpendicularly from and fixedly attached to said top face of said shuttle lock latch.

6. The prosthetic connector according to claim 5, wherein said plunger assembly comprises a plunger rod and a push-button member fixedly attached to at the distal end of said plunger rod, said plunger rod extending through said through-bore of said first section, whereby urging said plunger assembly downwardly displaces said shuttle lock latch.

7. The prosthetic connector according to claim 1, wherein said second section has a generally planar rear surface and a semi-toroidal front surface; wherein said planar rear surface is positioned in the interior of said housing and said semi-toroidal front surface forms the front of said housing.

8. The prosthetic connector according to claim 1, wherein said bottom surface of said elongated recess includes a spring-receiving bore therein along said diameter, said spring member extending into said spring receiving bore, wherein said spring member can be compressed into said spring-receiving bore.

9. The prosthetic connector according to claim 1, further including attachment means to attach said first section to said second section.

* * * * *